(12) United States Patent
Lewandowski et al.

(10) Patent No.: US 6,487,343 B1
(45) Date of Patent: Nov. 26, 2002

(54) FIBER OPTIC LIGHT MIXER

(75) Inventors: Mark S. Lewandowski, Hutchinson, MN (US); Kenneth R. Quast, Hutchinson, MN (US); Dean E. Myers, Stewart, MN (US); Mark A. Schmidt, Darwin, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 0 days.

(21) Appl. No.: 09/585,144

(22) Filed: Jun. 1, 2000

Related U.S. Application Data

(60) Provisional application No. 60/137,390, filed on Jun. 3, 1999.

(51) Int. Cl.[7] .................................................. G02B 6/26
(52) U.S. Cl. ............................. 385/51; 385/24; 385/28; 385/32
(58) Field of Search .......................... 385/51, 24, 28, 385/32, 46, 43, 48, 27, 30, 52

(56) References Cited

U.S. PATENT DOCUMENTS

| | | | |
|---|---|---|---|
| 3,874,781 A | 4/1975 | Thiel | 350/96 C |
| 4,910,539 A | 3/1990 | Mathis et al. | 350/96.15 |
| 5,212,748 A | 5/1993 | Curtiss et al. | |
| 5,224,478 A | 7/1993 | Sakai et al. | |
| 5,339,375 A | 8/1994 | Kerns | |
| 5,400,421 A | * 3/1995 | Takahashi | 385/24 |
| 5,548,672 A | * 8/1996 | Hattori et al. | 385/43 |
| 5,584,296 A | 12/1996 | Cui et al. | |
| 5,879,294 A | 3/1999 | Anderson et al. | |
| 5,978,534 A | * 11/1999 | O'Rourke et al. | 385/52 |

FOREIGN PATENT DOCUMENTS

| | | |
|---|---|---|
| EP | 0 476 596 | 3/1992 |
| EP | 0 800 099 | 10/1997 |
| EP | 0 816 829 | 1/1998 |
| GB | 1 386 734 | 3/1975 |
| GB | 1 558 643 | 1/1980 |

* cited by examiner

*Primary Examiner*—Mohammad Sikder
(74) *Attorney, Agent, or Firm*—Faegre & Benson LLP

(57) ABSTRACT

An optical structure for combining light from a plurality of individual optical fibers into a single optical transmission device. The structure can be incorporated into the optical probe of a spectrophotometric instrument and includes a plurality of optical send fibers having input and output ends and an optical light mixer having input and output ends. The output ends of the send fibers are secured in optical communication with the input end of the light mixer.

10 Claims, 11 Drawing Sheets

FIBER OPTIC LIGHT MIXER

REFERENCE TO RELATED APPLICATIONS

1. This application claims the benefit of U.S. Provisional Application Serial No. 60/137,390 filed on Jun. 3, 1999 and entitled "Fiber Optic Light Mixer."

2. Reference is hereby made to the following commonly assigned and copending U.S. Patent Applications which are incorporated herein by reference:

i). Ser. No. 09/584,990 filed on Jun. 1, 2000 and entitled "Calibration Mode Recognition And Calibration Algorithm For Spectrophotometric Instrument."

ii). Ser. No. 09/584,862 filed on Jun. 1, 2000 and entitled "Disposable Tissue Probe Tip."

FIELD OF THE INVENTION

The present invention is a light mixer for use in connection with an optical probe of a spectrophotometric-type instrument. In particular, the invention is a mixer for combining the different wavelength light beams from a plurality of discrete optical fibers into a homogeneous beam prior to transmission into tissue being analyzed.

BACKGROUND OF THE INVENTION

Spectrophotometric-type instruments are known and used in a variety of applications. An instrument of this type is, for example, disclosed in the Anderson et al. U.S. Pat. No. 5,879,294. These instruments transmit light at a number of predetermined wavelengths through the tissue being measured, and then collect and process the light. Measurements of the tissue parameters of interest are generated as a function of the attenuation of the light at these wavelengths by the tissue. Several different approaches for obtaining the different wavelength light signals are used. One approach is to transmit through and collect from the tissue broad bandwidth light, and to separate the different wavelength signals from the collected light prior to processing. Another approach is to use light emitting diodes (LEDs) or other sources to generate narrow bandwidth light beams (i.e., signals at the wavelengths of interest). These narrow bandwidth beams are then individually transmitted to the tissue being measured by separate individual optical fibers sometimes referred to as send fibers. A drawback of the use of individual send fibers is that light from one or more of these fibers may be attenuated differently than the light from other fibers due to inhomogeneities on the surface of the tissue where the light exits the send fibers and is transmitted into the tissue (i.e., the tissue target). This drawback is possible even though the ends of the send fibers are located adjacent to one another. For example, the end of one of the fibers could be over a mole or hair, while the others are not. Inaccurate measurements can result from these circumstances.

A number of approaches for combining light from individual optical fibers are known. One approach is to fuse the individual fibers into a common fiber. Another approach is to fixture the LEDs onto an integrating sphere which mixes the light. An optical fiber at the exit port of the integrating sphere transports the light to the tissue target. Yet another method is to utilize the waveguide effect of semiconductor and other materials.

There remains, however, a continuing need for improved light mixers for use with spectrophotometric instruments. A light mixer which can effectively mix narrow bandwidth light from several optical fibers would be desirable. To be commercially viable the light mixer should be capable of being efficiently manufactured.

SUMMARY OF THE INVENTION

The present invention is an improved light mixer structure for combining light from a plurality of individual optical fibers into a single optical transmission device. One embodiment of the light mixer structure includes a plurality of optical send fibers having input and output ends and an optical mixer having input and output ends. The output ends of the send fibers are in optical communication with the input end of the light mixer. The light mixer provides a high degree of light mixing yet is capable of being efficiently manufactured.

DETAILED DESCRIPTION OF THE PREFERRED EMBODIMENTS

Figure 1:
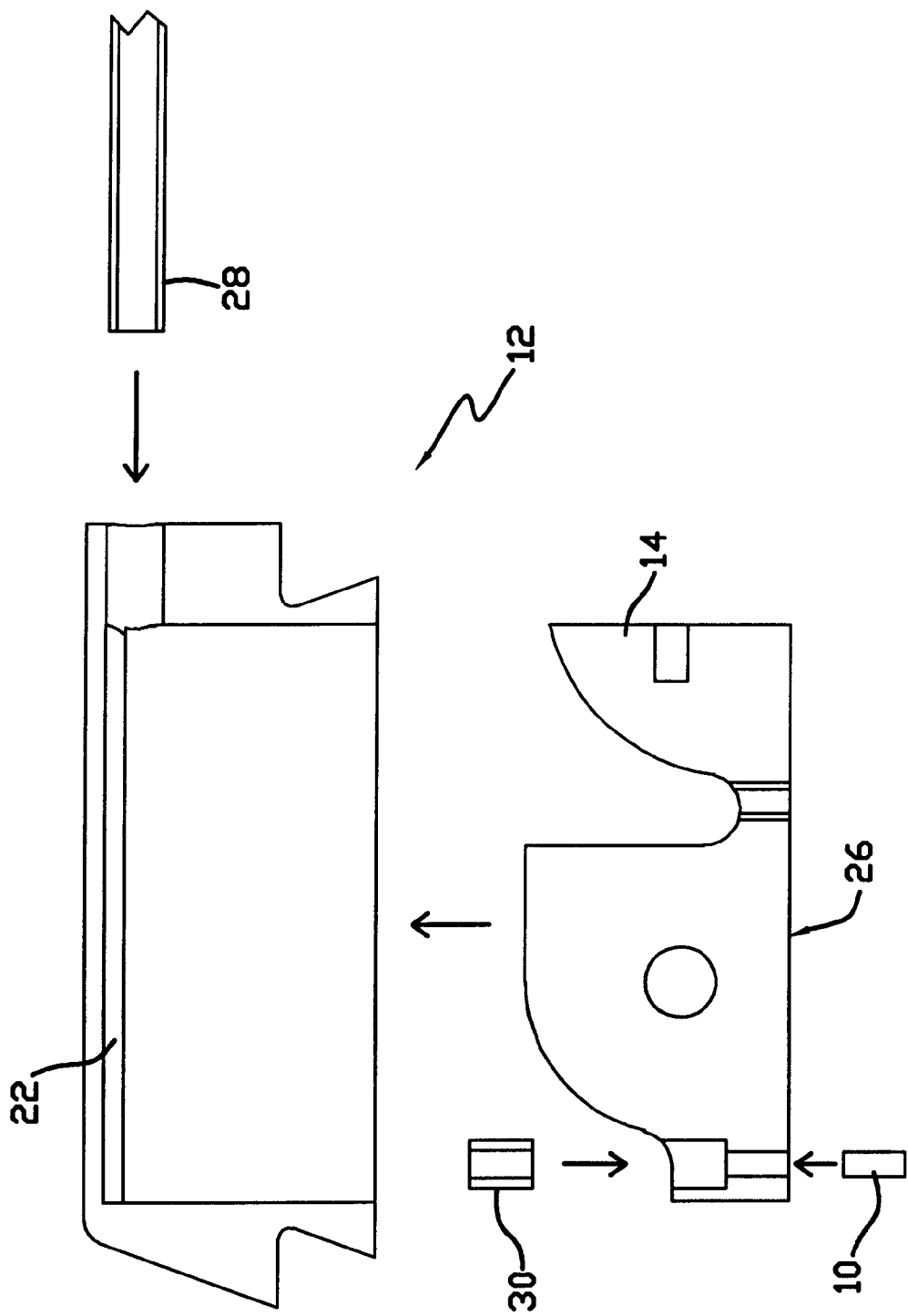
FIG. 1 is an exploded sectional side view of an embodiment of an optical probe and disposable tip which includes a light mixer in accordance with a first embodiment of the present invention.
Figure 2:
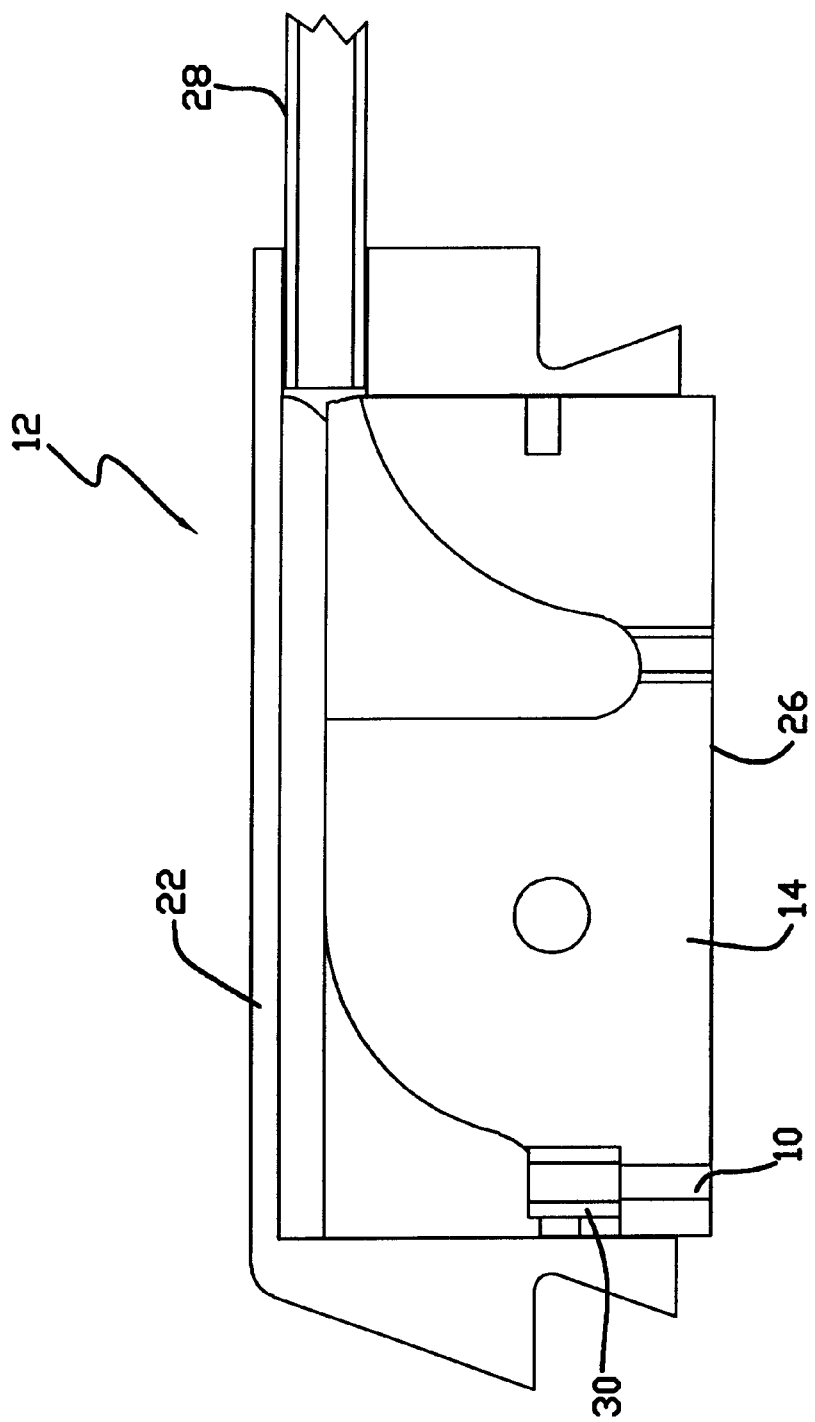
FIG. 2 is a sectional side view of the probe and light mixer shown in FIG. 1 without the optical fibers.
Figure 3:
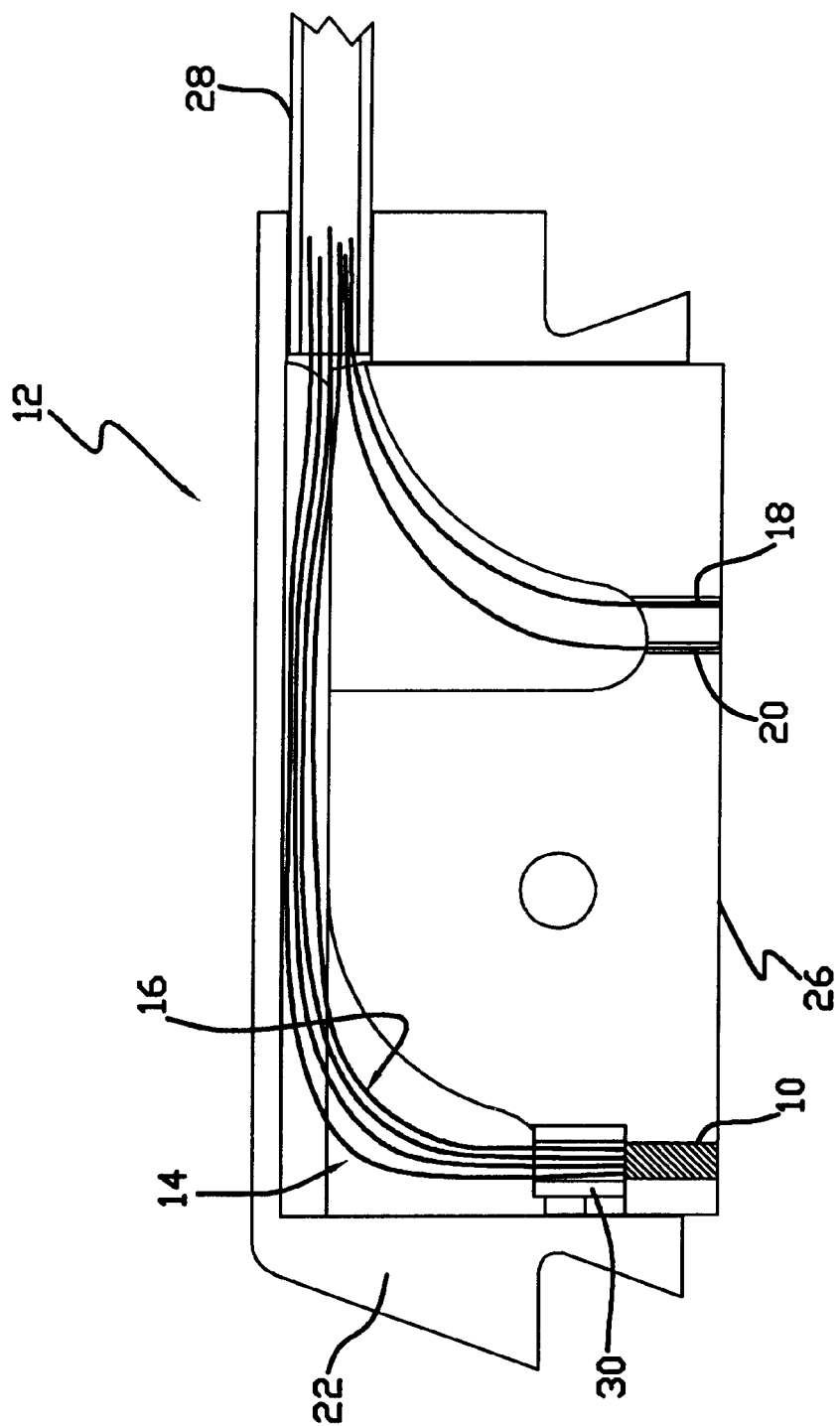
FIG. 3 is a sectional side view of the probe and light mixer shown in FIG. 1 with the optical fibers.
Figure 4:
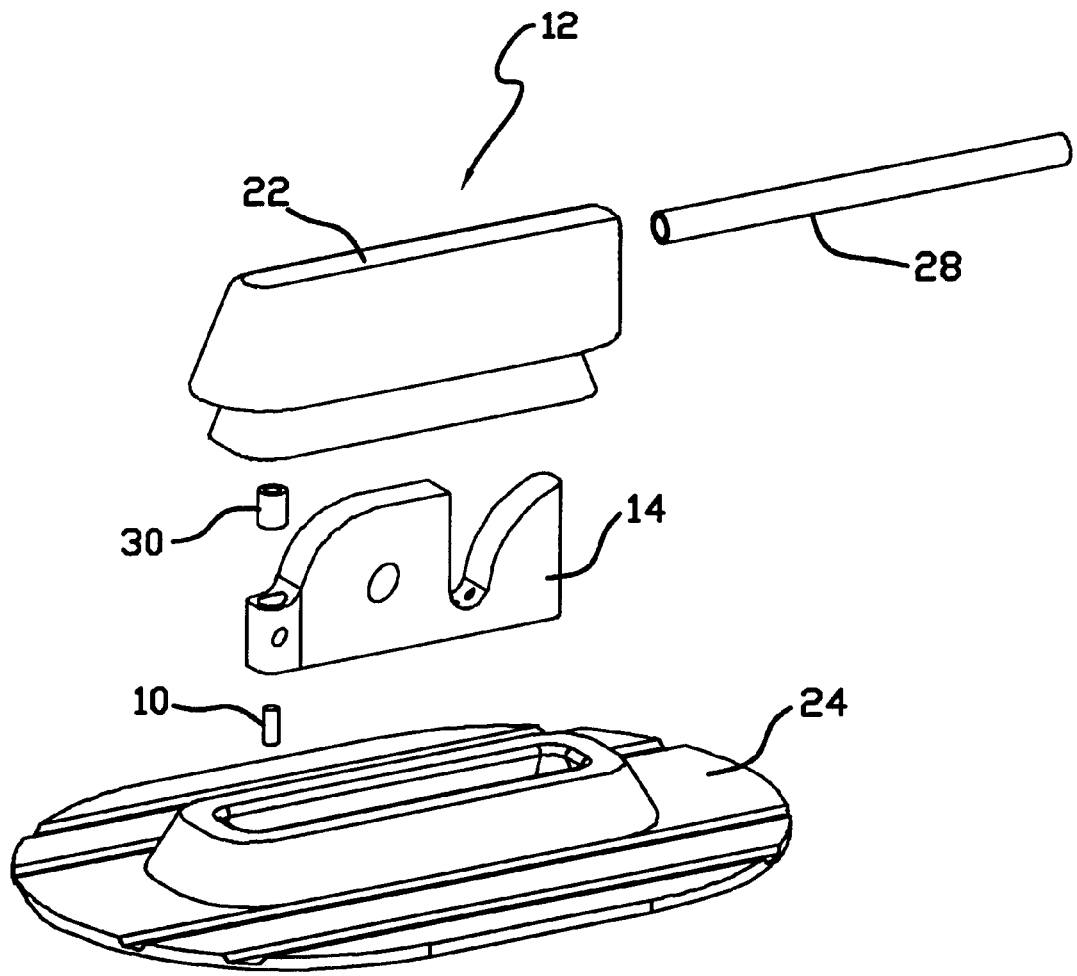
FIG. 4 is an exploded isometric view of the probe and light mixer shown in FIG. 1 with a disposable tip, showing the upper surfaces of the components.
Figure 5:
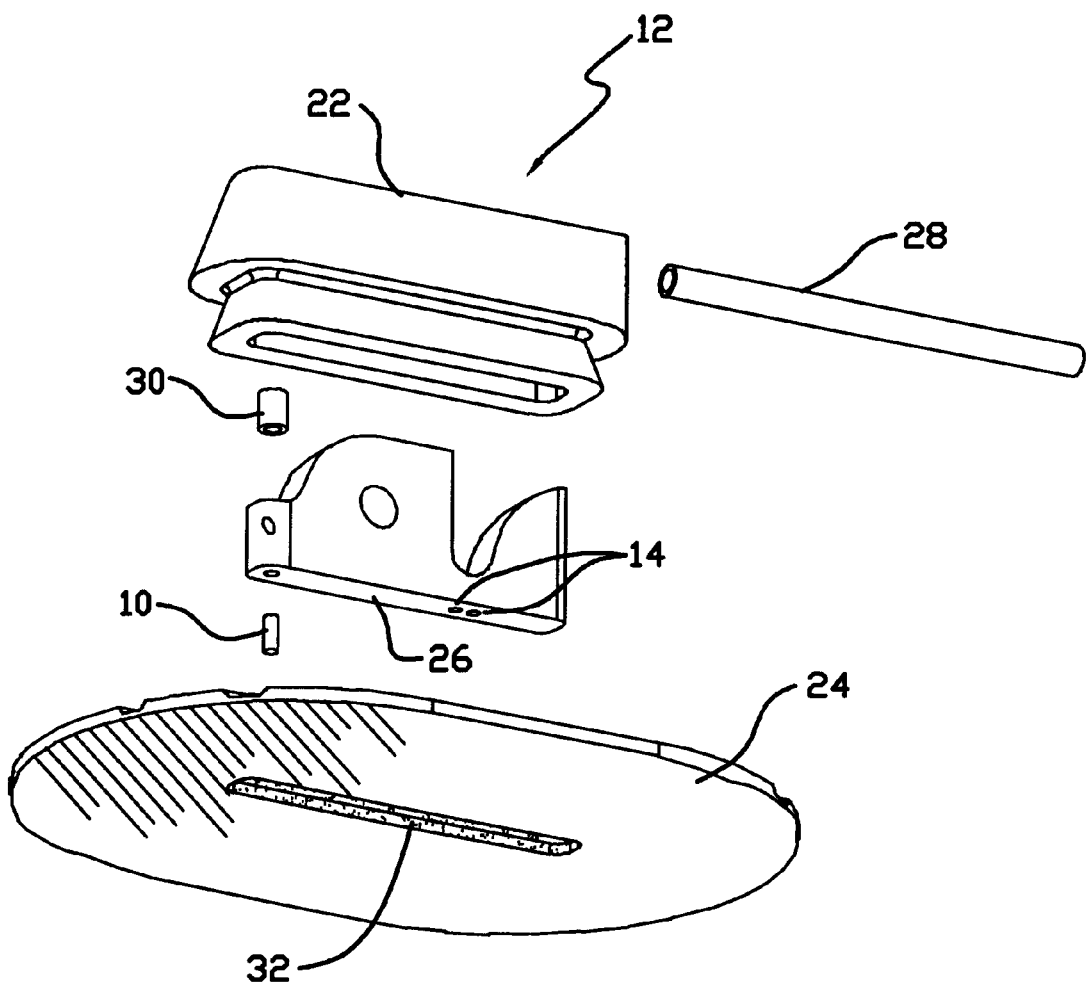
FIG. 5 is a an exploded isometric view of the probe and light mixer shown in FIG. 1 with a disposable tip, showing the lower surfaces of the components.
Figure 6:
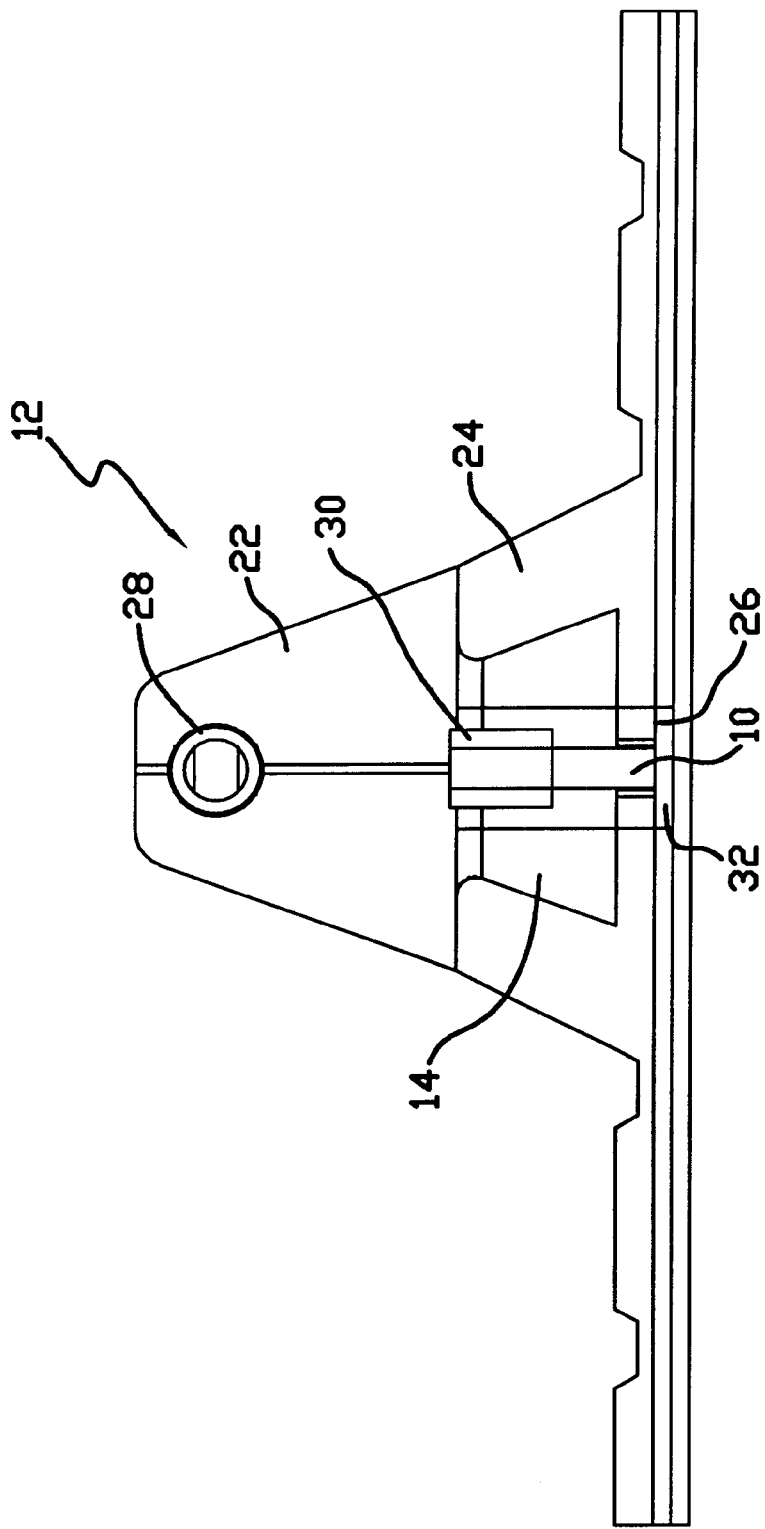
FIG. 6 is a sectional side view of the probe, light mixer and disposable tip shown in FIGS. 4 and 5.

FIGS. 1–6 illustrate an optical probe 12 which can be used in connection with the instrument shown in the Anderson et al. U.S. Pat. No. 5,879,294 and which includes a light mixer 10 in accordance with a first embodiment of the present invention. Briefly, and as shown, the probe 12 includes an insert 14 for holding a number of optical fibers 16, 18 and 20, a housing 22 into which the insert is mounted and a disposable elastomeric tip 24 which is releasably mounted to the housing. The optical fibers 16, 18 and 20, which terminate at a tissue-facing surface 26 of the tip insert 14, are coupled between the housing 22 and instrument (not shown) within a cable housing 28. The illustrated embodiment of the probe 12 has 4 send fibers 16 through which light of different wavelengths from the instrument (provided by narrow bandwidth LEDs) is transmitted to the probe. The ends of the send fibers 16 are sealed in a ferrule 30. The light mixer 10 is a section of optical fiber located between the fiber ferrule 30 and the tissue-facing surface 26 of the probe 12. The different wavelengths of light emitted from the ends of the send fibers 16 are mixed within the fiber of mixer 10 and thereby scattered throughout the surface area of the fiber at the tissue-facing surface 26. Each wavelength of light will thereby travel through a similar volume of tissue after being transmitted from the probe 12. As shown, a receive fiber 18 and a calibration recognition fiber 20 also have ends which terminate at the tissue-facing surface 26 of the probe 12. The receive fiber 18 collects light that has traveled through the tissue being analyzed and transmits the collected light to the instrument for processing. Light emitted from the calibration recognition fiber 20 is used by the instrument to control a calibration procedure in a manner described in the above identified related application entitled "Calibration Mode Recognition And Calibration Algorithm For Spectrophotometric Instrument."

Figure 7:
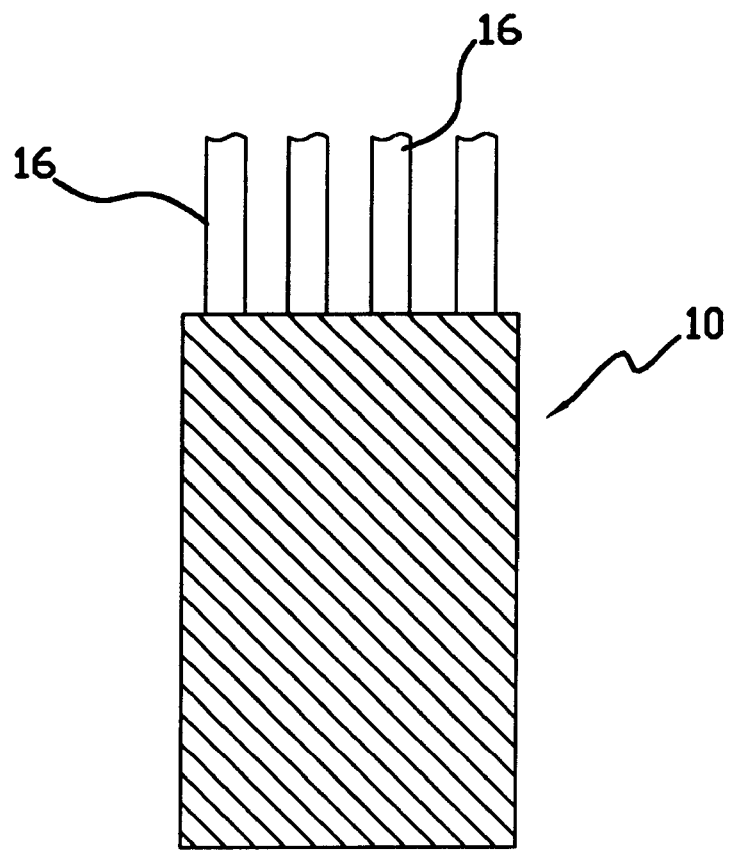
FIG. 7 is a sectional view of the light mixer and send optical fibers shown in FIGS. 1–6.
Figure 8:
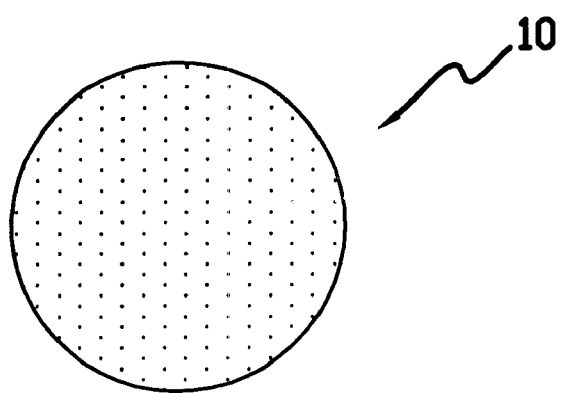
FIG. 8 is an end view of the light mixer shown in FIG. 7.

The light mixer 10 can be described with reference to FIGS. 1–8. The mixer 10 accepts, on its input side, light from the individual send fibers 16. The light mixer enhances the homogeneity of the light emitted on its output side and transmitted to the tissue. The result is that variations (e.g., in intensity) in wavelength of light transmitted from the mixer 10 vs. the position on the output end of the mixer are minimized. All wavelengths of the light entering the tissue will therefore be generally equally attenuated by the tissue, since a common entry point into the tissue will not bias any wavelength toward a longer or shorter path length than other wavelengths. This feature is illustrated diagrammatically in FIGS. 7 and 8 by the light ray reflections. Each wavelength of light is scattered over the whole cross-sectional area of the fiber of mixer 10, enabling each wavelength of light to travel through a similar volume of tissue.

In one embodiment of the invention the output end of the mixer 10 is in direct contact with the tissue being measured through the probe window 32. A curved segment of optical fiber (e.g., glass or plastic) with a numerical aperture (acceptance angle) greater than that of the send fibers 16 can be used for the mixer 10. Both ends of the mixer 10 can be polished clear. The output ends of the send fibers 16 can be in near direct contact (e.g., within about 0.025 mm) with the input side of the mixer 10. The output end of the mixer 10 can be polished flat with the probe tip 12. The minimum diameter of the mixer 10 should be such that it is larger than the overall packed diameter of the input fibers 16. End faces of the mixer 10 fiber can also be coated with an anti-reflective material to increase throughput. One benefit of the larger diameter mixer 10 over that of a single fiber is a reduction in the power density present at the entrance point to the tissue, and therefore reduced regulatory issues (e.g. because there is less potential to locally heat or burn the tissue).

The mixer 10 can be made from materials including glass and plastic fiber, and also have its faces angle polished. The mixing media need not necessarily be formed from fiber as it may take place in a free space area beyond where the fibers are recessed from the tissue-facing surface of the probe tip 12. Mixing can occur in a waveguide fashion prior to entering the tissue. As noted above, the mixer 10 can also reside in an area other than the probe tip 12. For example, it can be located in the cable housing 28, closer to the instrument itself However, the stiffness and bending radius of the cable assembly would then increase due to the presence of a larger diameter fiber. A plastic fiber can also be used, but if so it would be most advantageous in small lengths due to its attenuation properties at wavelengths typically used in spectrophotometric instruments. It is not necessary that the mixer 10 be larger in diameter than the send fibers 16 or that it have a larger numerical aperture, but the intensity of light transmitted from the output of the mixer would be reduced under these circumstances. Similarly, an anti-reflective coating need not be present on the mixer 10, but throughput efficiency would likely be reduced without such a coating.

A number of approaches can be used to manufacture the light mixer 10. For example, the ends of the send fibers 16 can be secured in the combiner ferrule 30 with an optically-suitable epoxy and cured. The combiner ferrule 30 can then be cleaved and polished. The mixer 10 fiber can be cut to its desired approximate length and one end polished. The polished end can then be mounted to the polished end of the combiner ferrule 30 using epoxy adhesive. The output end of the mixer 10 fiber is mounted to the distal tip insert 14, for example with epoxy adhesive, and then cured. Finally, the distal end of the mixer 10 fiber on the tissue-engaging face 26 of the probe 12 can be cleaved and polished.

Figure 9:
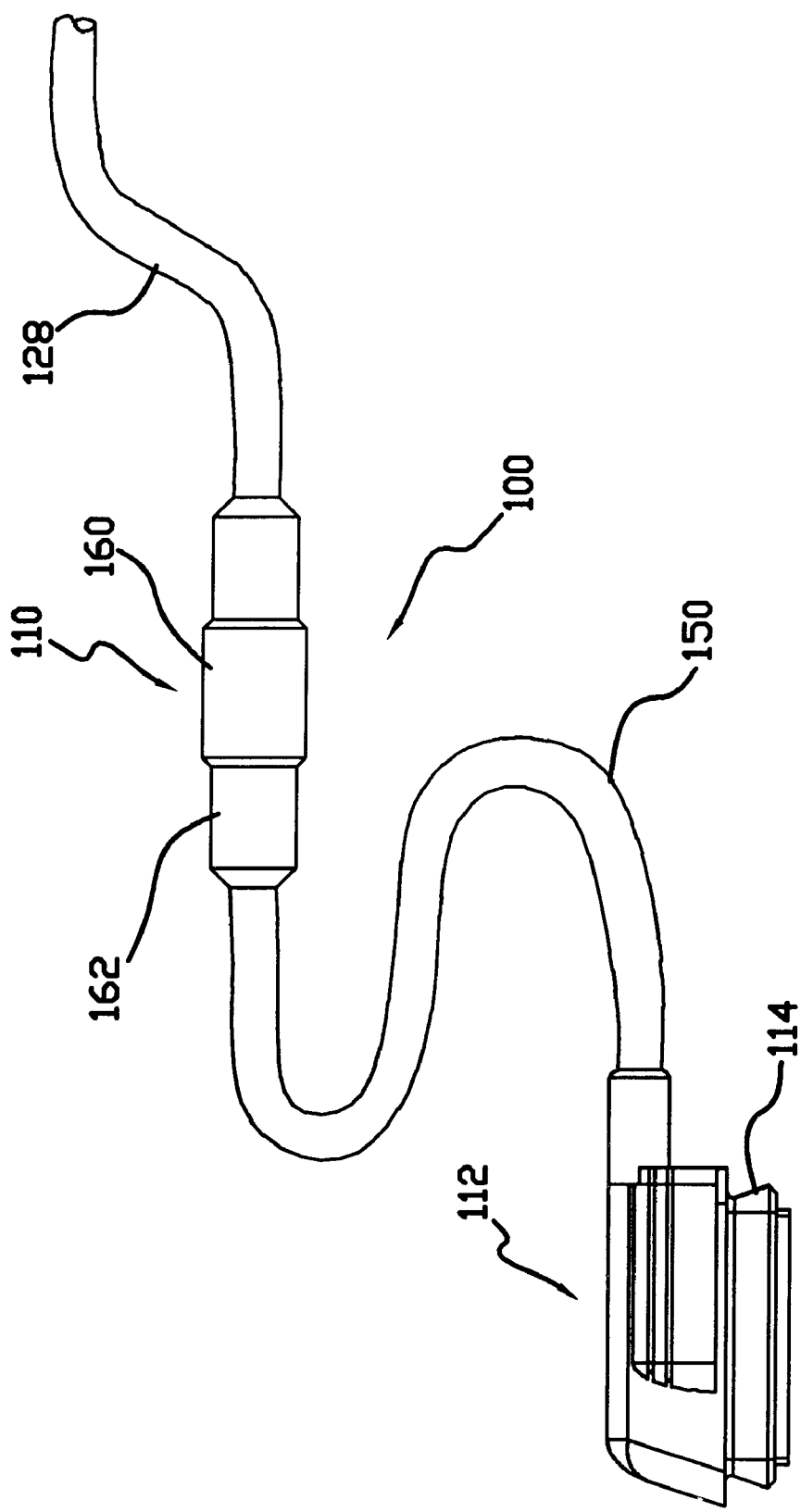
FIG. 9 is a side view of a probe including a light mixer in accordance with a second embodiment of the present invention.
Figure 10:
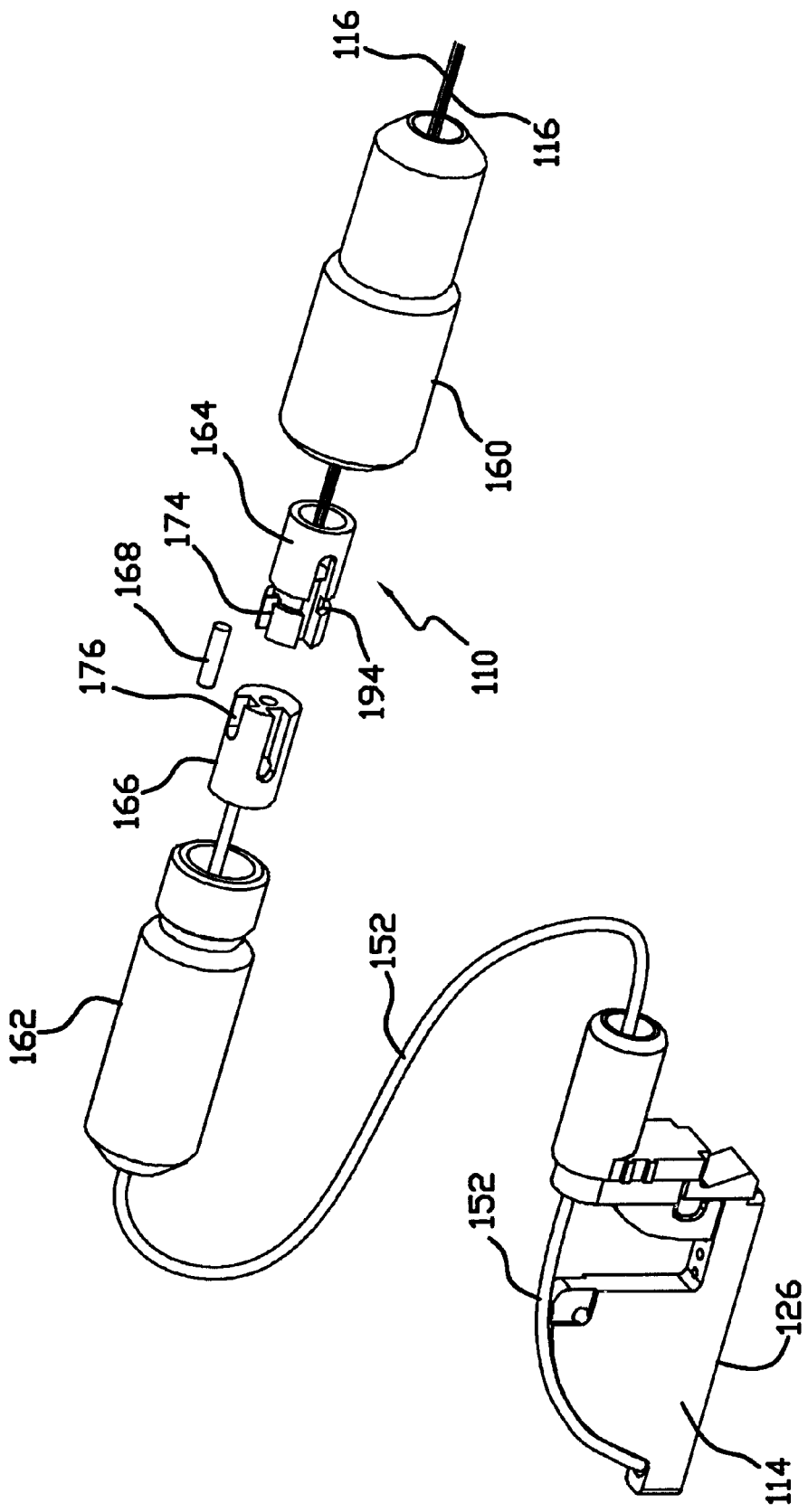
FIG. 10 is an isometric view of the probe shown in FIG. 9 with the light mixer assembly shown in exploded form.
Figure 11:
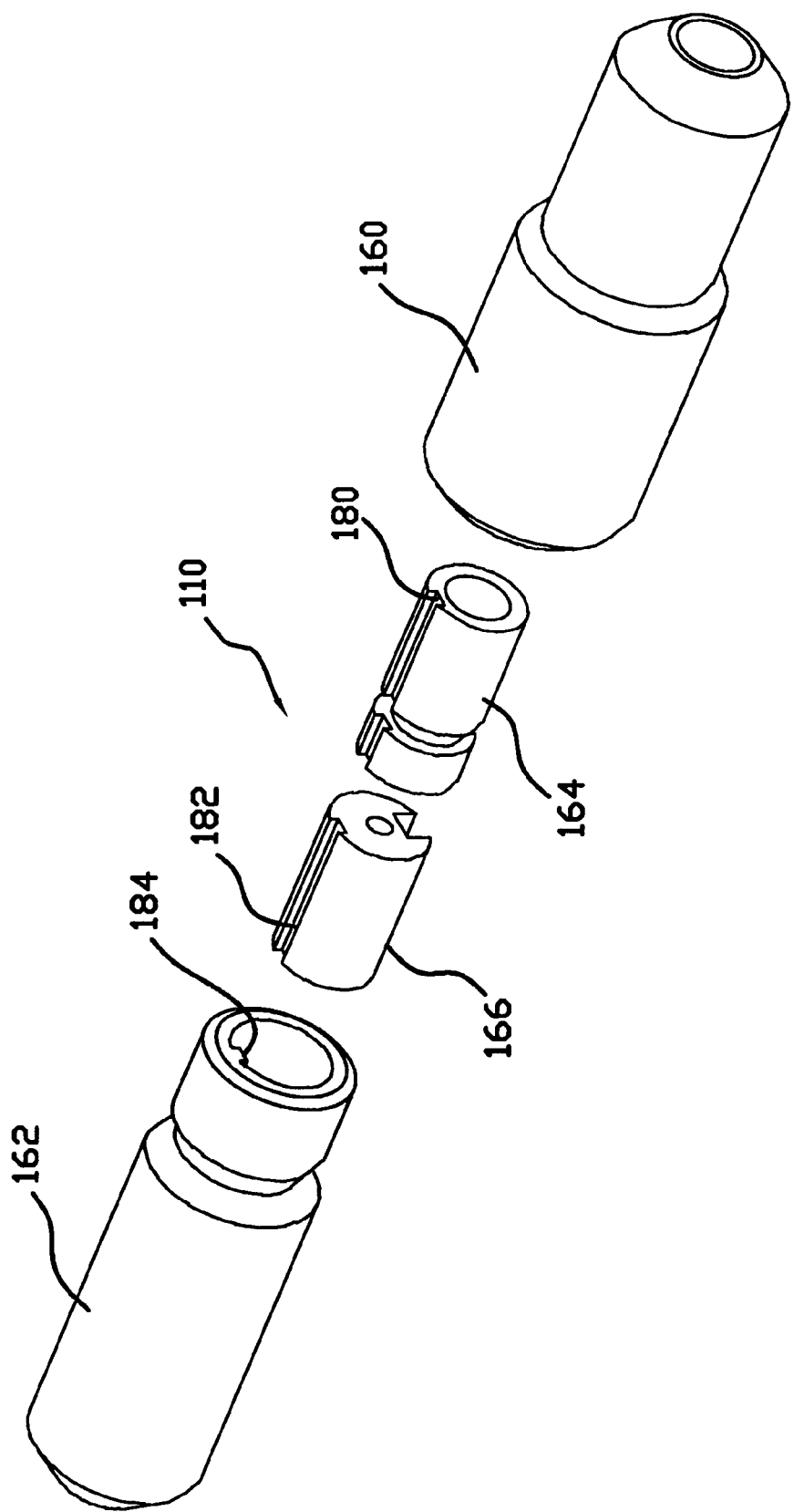
FIG. 11 is a detailed exploded isometric view of the probe shown in FIG. 10.
Figure 12:
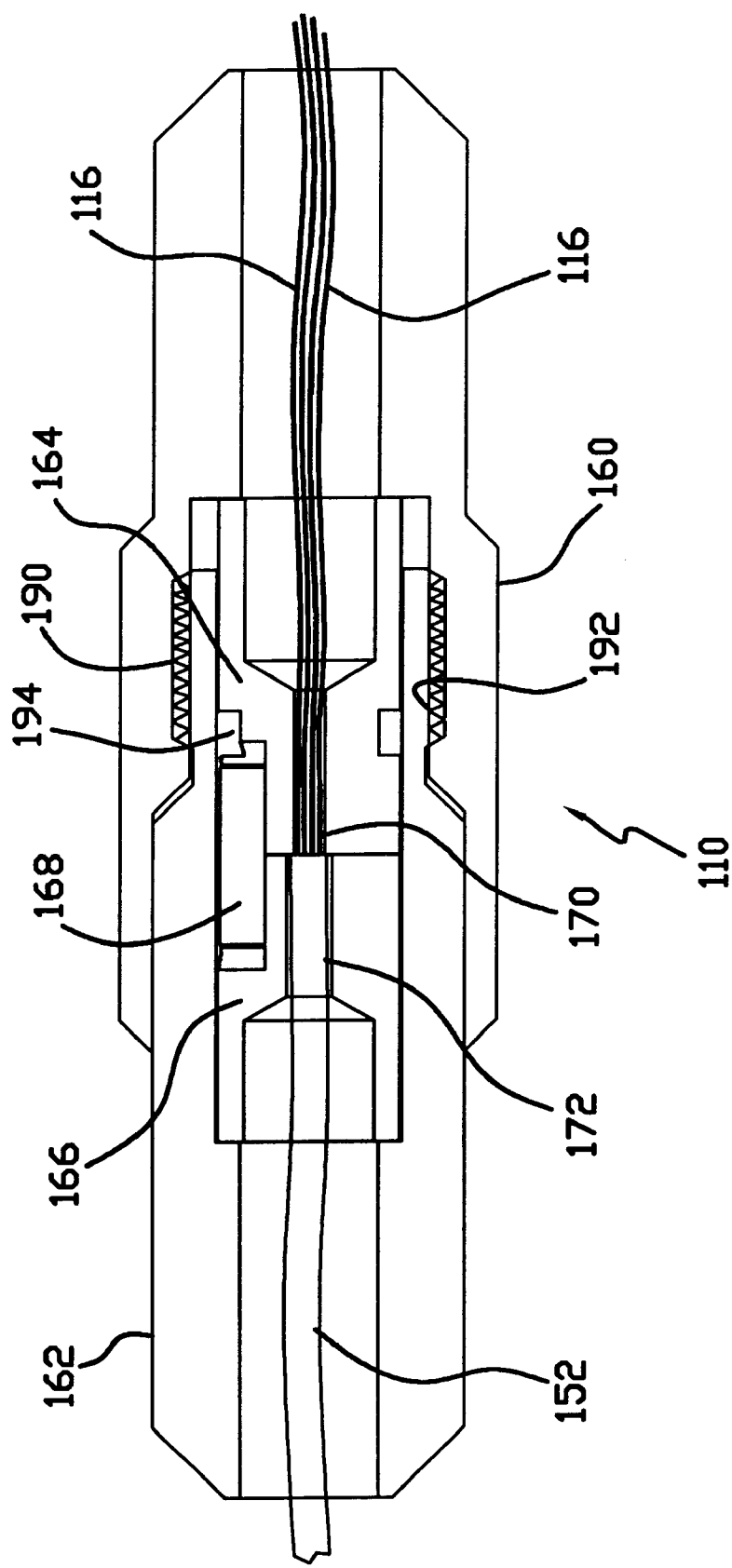
FIG. 12 is a sectional side view of the light mixer assembly shown in FIGS. 9–11.

A probe assembly 100 which includes a light mixer assembly 110 and probe tip 112 in accordance with a second embodiment of the present invention can be described with reference to FIGS. 9–12. The assembly 100 includes a cable housing 128 through which a plurality of send fibers 116 extend between the light mixer assembly 110 and light sources (not shown). In one embodiment the length of the send fibers 116 within the cable housing 128 is about 270 cm. A second cable housing 150 houses a mixer fiber 152 which extends between the assembly 110 and the tissue facing surface 126 of the probe insert 114. Mixer fiber 152 is about 30.5 cm long in one embodiment of the invention. The light mixer assembly 110 effectively splices the send fibers 116 to the mixer fiber 152 and includes a connector formed by outer shell 160, inner shell 162, send fiber ferrule 164, mixer fiber ferrule 166 and alignment pin 168. The send fibers 116 extend through the connector outer shell 160 and into send fiber ferrule 164. The ends of the send fibers 116 are secured (e.g., by an optical grade adhesive) in an aperture 170 in the send fiber ferrule 164, cleaved, and polished to provide an optical-quality mating surface. Similarly, the end of the mixer fiber 152 extends through the connector inner shell 162 and into mixer fiber ferrule 166. The end of the mixer fiber 152 is located within an aperture 172 in the mixer fiber ferrule 166 and cleaved and polished to provide an optical-quality mating surface. Optical grade adhesive or other approaches can be used to secure the end of the mixer fiber 152 in the aperture 172 of the mixer fiber ferrule 166.

The faces of the ferrules 164 and 166 with the ends of send fibers 116 and mixer fiber 152, respectively, are aligned with one another, and relative rotational movement prohibited, by the alignment pin 168 which fits into slots 174 and 176 in the ferrules. Send fiber ferrule 164 includes a key alignment slot 180 which engages a key tab 184 within the inner shell 162 of the connector to align the ferrule and connector. Similarly, the mixer fiber ferrule 166 includes a key alignment slot 182 which also engages key tab 184 within the inner shell 162 of the connector to align the ferrule and connector. When closed on one another the inner and outer connector shells 162 and 160 urge the faces of the ferrules 164 and 166 with the ends of the fibers 116 and 152, respectively, into optical engagement with one another. Forces to retain the faces of the ferrules 164 and 166 in engagement with one another can be provided by mating threads 190 and 192 on the outer and inner connector shells 160 and 162, respectively. Epoxy or other adhesive can also be used to secure the connector shells 160 and 162 together and thereby optically engage the send fibers 116 with the mixer fiber 152. A tensile reinforcement fiber (e.g., a length of braided polyethylene line, not shown) extending through the cable housings 128 and 150 and through the mixer assembly 110 can be wrapped and tied around the circumferential groove 194 to provide a strain relief on the fibers 116 and 152.

The light mixer described herein has a greater efficiency (at least three to four times) than a 4:1 optical fiber combiner and waveguide material, and an approximately one-thousand times efficiency increase over integrating sphere approaches. The mixer is considerably less expensive to manufacture than known devices of the type described above. In addition to these advantages, the device is no larger in size than a fiber combiner and waveguide, but is considerably smaller than an integrating sphere.

The probe tip 24 is an elastomeric fixturing device which is used to reversibly attach the optical probe to a patient's tissue measurement site (e.g., the skin of a patient). One embodiment of the probe tip 24 is described in the above-referenced application entitled "Disposable Tissue Probe Tip." Briefly, the tip can be formed from a 1-piece elastomeric base member molded from flexible material such as silicone rubber (e.g., 50 shore A durometer from Applied Silicone) or polyethylene foam (e.g., Plastasote from Zotefoams Limited). Other suitable materials include isoprene/EPDM/nitrile rubbers, PVC, polyurethane, rubber alloys and vinyl acetate foams. An optically clear window (i.e., a window which transmits the light wavelengths of interest) separates the probe from the patient's skin, thereby functioning as a fluid/infection barrier. A pressure sensitive adhesive on the bottom or tissue-engaging surface of the base member holds the tip to the measurement site. Once removed from the patient's skin, the tip can be disposed. A probe-engaging recess in the base member is adapted to releasably secure the tip to the probe. The illustrated embodiment of the tip has a tapered cavity boot area which mates and fits snugly to the correspondingly tapered exterior surface of the tip housing. The described mating configuration enables the optical probe to be inserted into and removed from the tip without having to remove the tip from the patient.

In one embodiment the material of the tip is optically opaque and has mating surfaces which overlap the reusable probe tip in a manner to trap ambient light. The tip preferably prevents or minimizes the amount of ambient light entering the tissue being measured near the measurement site. This property is accomplished by the extended tissue-engaging surface of the base member from the window. The fixture can be molded with a saddle or other shape which enables it to conform to the curvature of the leg, arm or other anatomy of the patient.

A double-sided pressure sensitive adhesive can be bonded to the lower surface of the tip. Alternatively, the adhesive can be a transfer tape (unsupported pressure sensitive adhesive). A single coated tape (pressure sensitive adhesive on the tissue-engaging side only) could also be used if the support carrier can be heat laminated or otherwise bonded to the elastomeric member. The adhesive and any associated support substrates should be optically clear if they are also functioning as the window. Alternatively, a separate section of optically clear material which does not have adhesive properties can be mounted to the tip to function as the window. Such a window component can be fixtured within the cavity of the tip. For example, the window can be a thin (e.g., about 5 mil), thermoformed transparent (i.e., polyester, polyethylene or polycarbonate) plastic material molded to conform to the hole through the elastomeric tip member. The window can then be permanently mounted to the elastomeric base member by adhesive.

A release liner can be used to protect the adhesive and window while the tip is being stored prior to use. The liner should be designed to be easily pulled off the tip to expose the pressure sensitive adhesive. The release liner can also be formed from optically clear materials, thereby allowing the tip to be used intermittently on a patient before the release liner is removed and the tip is fixedly mounted to the patient for continuous measurements. Alternatively, a non-transparent paper release liner can be used if the adhesive component is not designed to provide the window between the tip and probe.

Structural approaches other than the elastomeric interference fit described above can be used to releasably secure the tip to the optical probe. For example, snap-type or other buttons or latch mechanisms can be used for this purpose.

The probe tip does not permanently fixture the optical components of the probe within a "patient sensor." Instead, the optical (and relatively expensive and functionally reusable) components can be removed from the patient without affecting the attachment of the tip to the patient. This reversibility of the probe connection to the patient allows the probe to be disconnected and reused on the same patient without having to issue a new disposable tip. In situations where a patient is temporarily removed from the instrument (e.g., for x-ray or surgery), the tip can remain attached to the patient and measurement later resumed.

In conclusion, the present invention is a light mixer for use in connection with a spectrophotometric-type instrument having a plurality of optical send fibers for transmitting narrow bandwidth light of different wavelengths. The light mixer efficiently combines the light from the individual fibers into a generally homogeneous beam for transmission into the tissue being measured. In one embodiment described herein, the light mixer is located in the probe used to transmit the light into the tissue. In other embodiments the light mixer can be positioned at other locations between the probe and the LEDs or other sources of the narrow bandwidth light.

Although the present invention has been described with reference to preferred embodiments, those skilled in the art will recognize that changes can be made in form and detail without departing from the spirit and scope of the invention.

What is claimed is:

1. An optical structure for combining light from a plurality of individual optical fibers into a single optical transmission device, including:

a plurality of optical send fibers having input and output ends and diameters, for transmitting light from the input ends to the output ends;

an optical light mixer having input and output ends and configured to receive and mix the light from the send fibers and transmit the mixed light from the input end through the output end onto a target; and structure for securing the output ends of the send fibers in optical communication with the input end of the light mixer, the output end of the light mixer being sized to transmit light out of the mixer at a power density no higher than the power density of light received from at least one of the send fibers.

2. The optical structure of claim 1 wherein the structure for securing the send fibers to the light mixer includes adhesive.

3. The optical structure of claim 1 and further including a ferrule encompassing the output ends of the send fibers.

4. The optical structure of claim 3 and further including adhesive for securing the output ends of the send fibers within the ferrule.

5. The optical structure of claim 4 wherein the structure for securing the send fibers to the light mixer includes adhesive.

6. An optical tissue probe including the optical structure of claim 1 mounted thereto with the output end of the light mixer in communication with a tissue-facing surface of the probe.

7. The optical structure of claim 1 wherein the light mixer includes an optical fiber.

8. The optical structure of claim 7 and further including:
a send fiber ferrule for encompassing the output ends of the send fibers;
a mixer fiber ferrule for encompassing the input end of the light mixer ferrule; and
a housing for joining the send fiber ferrule and the mixer ferrule and to urge the output ends of the send fibers into optical communication with the input end of the light mixer.

9. The optical structure of claim 1 wherein each of the send fibers transmits light having a different wavelength.

10. The optical structure of claim 7, wherein the optical fiber has a circular cross-section.

* * * * *